United States Patent
Batzinger et al.

(12) 
(10) Patent No.: US 6,545,469 B1
(45) Date of Patent: Apr. 8, 2003

(54) EMBEDDED EDDY CURRENT INSPECTION APPARATUS, SYSTEM, AND METHOD

(75) Inventors: Thomas James Batzinger, Burnt Hills, NY (US); Shridhar Champaknath Nath, Niskayuna, NY (US); Kenneth Gordon Herd, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/682,902

(22) Filed: Oct. 31, 2001

(51) Int. Cl.[7] .............................................. G01N 27/90
(52) U.S. Cl. ...................... 324/238; 324/219; 324/232; 324/242
(58) Field of Search .............................. 324/219, 232, 324/238, 240–243, 261, 262

(56) References Cited

U.S. PATENT DOCUMENTS

| | | | |
|---|---|---|---|
| 5,321,358 A | * | 6/1994 | Mohr et al. |
| 5,389,876 A | | 2/1995 | Hedengren et al. ........ 324/242 |
| 5,510,709 A | | 4/1996 | Hurley et al. ............... 324/242 |
| 5,659,248 A | * | 8/1997 | Hedengren et al. ........ 324/242 |
| 5,793,206 A | * | 8/1998 | Goldfine et al. ............ 324/242 |

FOREIGN PATENT DOCUMENTS

| | | | |
|---|---|---|---|
| GB | 886247 | * 1/1962 | ................. 324/238 |
| SU | 700830 | * 11/1979 | ................. 324/238 |
| WO | 9840732 | 9/1998 | |
| WO | 0122076 | 9/2000 | |

OTHER PUBLICATIONS

U.S. patent application No. 09/627,049, Batzinger et al, "Method and Apparatus for Inspecting Components." (RD–27,963) filed Jul. 27, 2000.

* cited by examiner

*Primary Examiner*—Gerard R. Strecker
(74) *Attorney, Agent, or Firm*—Penny A. Clarke; Patrick K. Patnode

(57) ABSTRACT

An embedded eddy current inspection apparatus includes a substrate having an opening, and a test eddy current coil ("test coil") affixed to the substrate near the opening. An internally inspected multilayer component structure includes an upper layer, a lower layer, and an eddy current probe embedded between the upper and lower layers. The eddy current probe includes the test coil facing a subject layer selected from the upper and lower layers. A method of inspecting a multilayer component structure includes simultaneously energizing the test coil and a reference eddy current coil ("reference coil") embedded between the upper and lower layers and facing the subject layer. The reference coil is located in a reference region of the multilayer structure. A test signal from the test coil is compared with a reference signal from the reference coil, to determine whether a flaw is present in the subject layer near the test coil.

23 Claims, 5 Drawing Sheets

EMBEDDED EDDY CURRENT INSPECTION APPARATUS, SYSTEM, AND METHOD

BACKGROUND OF INVENTION

The present invention relates generally to eddy current inspection and, more particularly, to eddy current inspection of aircraft structures near fasteners.

Aircraft structures are generally constructed using multiple layers of material utilizing lap joints and fasteners, such as rivets. Sealants are often disposed between the layers to prevent corrosive materials from collecting in the joint. In response to stress exerted on the aircraft structure during operation, cracks occasionally develop in the layers comprising the aircraft structure in the vicinity of the fasteners.

In order to ensure the structural integrity of the aircraft, aircraft structures are repeatedly inspected during the life of the aircraft, to determine that cracks have not formed near the rivet hole. However, these inspections can be difficult to perform, due to the reduced access to critical inspection areas, such as portions of the aircraft structure surrounding the rivets. The inspections are further complicated by the fact that cracks internal to lap joints can be very difficult to detect.

Currently, aircraft structures are inspected for cracks internal to lap joints using x-ray, eddy current, and ultrasonic inspection techniques applied to the external surfaces of the lap joints. However, application of these inspection techniques is often impeded by the internal structure of the aircraft and frequently requires considerable aircraft disassembly. In addition, ultrasonic signals can be difficult to interpret because of the complicated geometry near the rivet and the number of interfaces in the lap joint. Eddy current inspection may undesirably require removal of the rivet and disassembly of the structure and is further complicated by the presence of sealants in the joints. X-ray inspection creates radiation exposure problems and requires evacuation of operators during testing, preventing concurrent maintenance and inspections.

By way of further background, eddy current inspection is based on the principle of electromagnetic induction in which a drive coil is employed to induce eddy currents within the material under inspection, and secondary magnetic fields resulting from the eddy currents are detected by a sense coil, generating signals which are subsequently processed. Eddy current inspection detects flaws as follows. The presence of a discontinuity or a crack in the surface of the component under inspection changes the flow of the eddy currents within the test specimen. The altered eddy current, in turn, produces a modified secondary magnetic field, which is detected by the sense coil, thereby generating a signal which indicates the presence of the flaw upon subsequent processing.

Previous eddy current inspection applications to aircraft structure involved positioning a single eddy current coil probe adjacent to the surface of the aircraft structure. Although this technique is adequate for external and easily accessible surfaces, it is not desirable for interior surfaces. Due to gaps between aircraft structure layers filled with air or sealants, low frequency eddy current inspection must be used to inspect interior surfaces from an external position. However, low frequency eddy current inspection provides limited resolution. Thus, in order to perform high resolution eddy current inspection of interior surfaces of a lap joint using this technique, the rivets would have to be removed and the structure disassembled. Accordingly, inspection times would be considerable to disassemble, inspect, and reassemble the aircraft structure. Further, the cost of labor required to perform these tasks would be high.

Moreover, the conventional eddy current inspection technique is performed during maintenance periods when the aircraft is taken out of use, disassembled, inspected, and reassembled. In particular, this conventional technique does not inspect for crack formation during flight operations.

Accordingly, it would be desirable to provide a method and apparatus for performing eddy current inspection on interior surfaces of multilayer structures that does not require disassembly of the multilayer structure. In addition, it would be desirable to provide a method and an apparatus for performing eddy current inspection on a lap joint near a fastener, that does not require disassembly of the fastener or the lap joint. It would further be desirable for the method and apparatus to permit periodic eddy current inspection of the lap joints and other multilayer structures, that provides information about the presence and size of cracks, such as cracks near fasteners (e.g., rivets) in the multilayer structure. In addition it would be desirable to provide a method and apparatus for performing eddy current inspection during flight operations.

SUMMARY OF INVENTION

Briefly, in accordance with one embodiment of the present invention, an embedded eddy current inspection apparatus includes a substrate having an opening, and a test eddy current coil affixed to the substrate near the opening.

In accordance with another embodiment, an internally inspected multilayer component structure includes an upper layer and a lower layer. The multilayer component structure further includes an eddy current probe embedded between the upper and lower layers. The eddy current probe includes a test eddy current coil facing a subject layer selected from the upper and lower layers.

In accordance with another embodiment, a method of inspecting a multilayer component structure including an upper and a lower layer is provided. The inspection method includes energizing a test eddy current coil embedded between the upper and lower layers. The test eddy current coil faces a subject layer selected from the upper and lower layers. The inspection method further includes energizing a reference eddy current coil simultaneously with the test coil. The reference eddy current coil is embedded between the upper and the lower layers in a reference region of the multilayer structure and faces the subject layer. The inspection method further includes comparing a test signal from the test eddy current coil with a reference signal from the reference eddy current coil, to determine whether a flaw is present in the subject layer near the test eddy current coil.

In accordance with another embodiment of the invention, an embedded eddy current inspection system is provided for inspecting a multilayer component structure including an upper and a lower layer. The inspection system includes an eddy current probe embedded between the upper and lower layers. The eddy current probe includes at least one test eddy current coil. The system further includes a signal generator configured to energize the test eddy current coil. The system also includes a comparison module for comparing a test signal received from the test coil and a reference signal and outputting a compared signal.

BRIEF DESCRIPTION OF DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
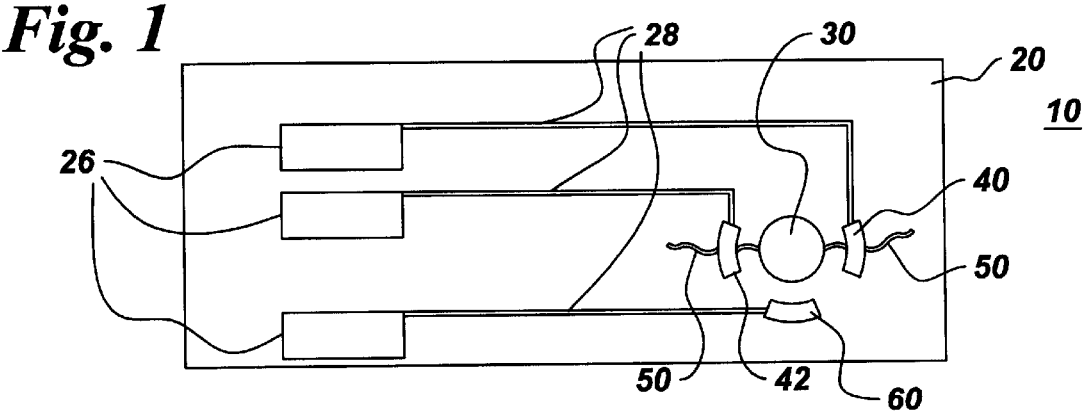
FIG. 1 is a top view of an embedded inspection apparatus according to one embodiment of the invention.

An embedded inspection apparatus 10 embodiment of the present invention is shown in FIG. 1. For reference purposes only, cracks 50 of an adjacent component layer (not shown) are indicated in FIG. 1, even though these cracks are not part of the embedded inspection apparatus 10. The embedded inspection apparatus is configured for embedding in a multilayer component structure 100, as illustrated for example in FIG. 4.

The embedded inspection apparatus 10 includes a substrate 20 with an opening 30, as illustrated in FIG. 1. The opening is configured to receive a fastener 70, such as a rivet. Other exemplary fasteners include bolts. An exemplary fastener is shown in cross-sectional view in FIG. 4. The embedded inspection apparatus further includes a test eddy current coil 40 (which is also referred to as a "test coil" herein) affixed to the substrate near the opening. The phrase "near the opening" means that the test coil is close enough to the opening that it can detect cracks 50 formed in an adjacent component layer 110 propagating outward from the fastener 70 extending through the opening and through the component layer. The precise distance between the test coil and the opening is determined by the engineering design criteria. For example, the shorter the allowable length of cracks extending from the fastener, the closer the test coil will be to the opening. However, an exemplary distance between the opening and the test coil is greater than about 0.5 mm.

Figure 2:
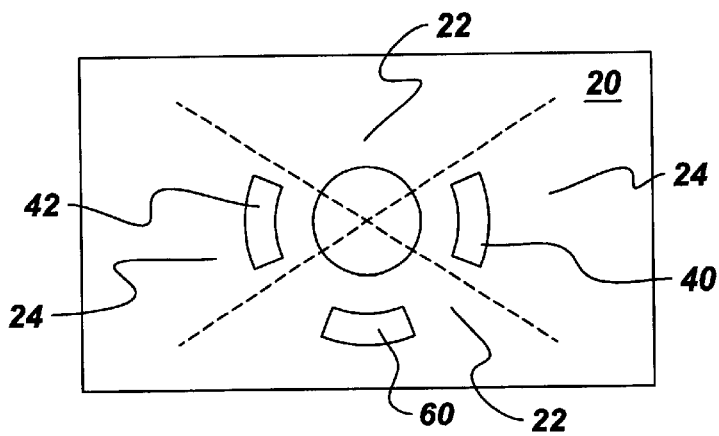
FIG. 2 depicts illustrative reference and testing areas.
Figure 10:
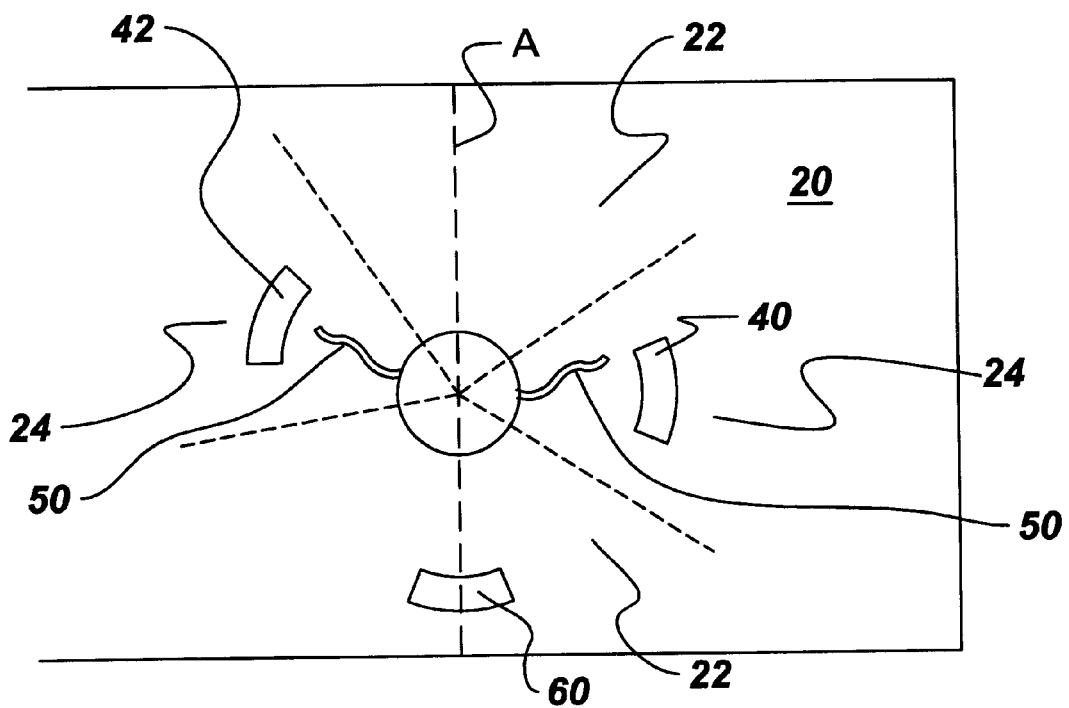
FIG. 10 depicts illustrative reference and testing areas.

According to one embodiment of the embedded inspection apparatus 10, the substrate 20 further includes a reference area 22. Exemplary reference areas are depicted in FIGS. 2 and 10. As suggested by the cracks 50 shown in FIG. 1, cracks in riveted component structures, such as the multilayer component structure illustrated in FIG. 4, preferentially form in certain directions based on the stresses on the component structures at the fastener (rivet) 70. Accordingly, testing and reference areas 24, 22 are designated on the substrate 20 around the opening 30 to correspond to the areas in which cracking can and cannot occur in the riveted component structure, respectively. As known to those skilled in the art, crack formation at a rivet hole is not necessarily reflectively symmetric about an axis A, shown for example in FIGS. 3 and 10. Rather, based on the position of the fastener relative to other fasteners and on any curvature of the aircraft structure near the fastener, crack formation may be asymmetric, as shown for example in FIG. 10. Accordingly, the test and reference areas 24, 22 are selected based on the engineering criteria for the desired application.

Where the substrate 20 includes a reference area 22, the embedded inspection apparatus 10 further includes a reference eddy current coil 60 (also referred to as a "reference coil" herein) affixed to the substrate and positioned in the reference area 22 near the opening 30. In addition, the test coil 40 is positioned in the testing area 24. An exemplary reference coil is positioned at about the same radial distance from the opening as the test coil. Advantageously, this exemplary configuration is approximately symmetric with respect to the fastener 70 extending through the opening. In this manner, the effect of the fastener on eddy currents detected by the test and reference coils are similar.

According to another embodiment, the embedded inspection apparatus 10 further includes an opposing test eddy current coil 42 (or "opposing test coil"), as shown in FIGS. 1 and 2. The opposing test coil is affixed to the substrate 20 near the opening 30 and is positioned across from the test coil 40. In this manner, the test coil and opposing test coils are configured to detect cracks on opposite sides of the opening. The phrase "across from the test coil" encompasses positions within the opposite test area 24. An exemplary opposing test coil is positioned approximately 180 degrees from the test coil, as illustrated in FIGS. 1 and 2. In addition, the exemplary opposing test coil is positioned at about the same radial distance from the opening as the test coil. However, as noted above, crack formation at a rivet hole is not necessarily symmetric about the axis A. Accordingly, the phrase "across from the test coil" further encompasses positions within an asymmetric opposite test area, as shown for example in FIG. 10. As noted above, the test areas are selected based on engineering criteria for the desired application.

Figure 3:
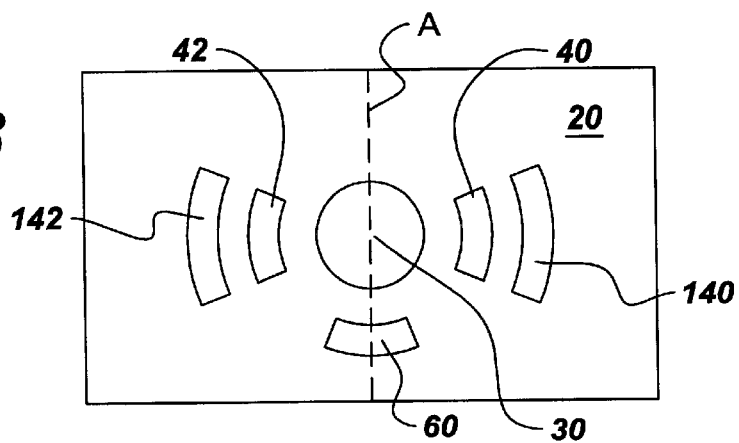
FIG. 3 is an enlarged view of the embedded inspection apparatus configured to monitor crack length.

In order to monitor the crack length, the embedded eddy current inspection apparatus 10 according to another embodiment further includes a second test eddy current coil 140 ("second test coil") affixed to the substrate 20 and positioned further from the center of the opening than is the test coil, as illustrated in FIG. 3. By the phrase "center of the opening," the center of area (or centroid) of the opening is meant. An exemplary second test coil is positioned radially outward from the test coil (i.e., essentially no rotation relative to the test coil), as shown in FIG. 3. However, where engineering criteria determine that the crack 50 will propagate in a non-radial fashion between the test and the second test coils, the second test coil is rotationally offset from the test coil by an amount determined by the engineering criteria.

In addition to the second test eddy current coil 140, the embedded eddy current inspection apparatus 10 further includes a second opposing test eddy current coil 142 ("second opposing test coil") affixed to the substrate 20 and positioned further from the center of the opening 30 than is the opposing test coil 42, as shown for example in FIG. 3.

Advantageously, the embedded eddy current inspection apparatus of this embodiment not only is configured to detect cracks 50 propagating outward from a fastener (not shown), but is further configured to monitor the length of the cracks. Depending on the engineering design criteria (namely, the allowable crack length), this principle can be extended to include third, fourth, fifth etc. sets of test coils (not shown) positioned still further from the center of the opening, in the manner shown in FIG. 3. For example, if the engineering design criteria specify an allowable crack length of less than about 2.5 mm, five pairs of test coils (not shown) spaced at about 0.5 mm intervals could be employed to monitor the crack length. However, those skilled in the art will readily recognize that both the number of pairs of test coils and spacing therebetween are purely illustrative and do not limit the embedded inspection apparatus of the present invention.

The substrate 20 is desirably formed of a flexible material, such as a flexible organic polymer. An exemplary flexible organic polymer is polyimide, one example of which is KAPTON®. KAPTON® is a federally registered trademark of E.I. du Pont de Nemours and Company of Wilmington, Del. An exemplary substrate has a thickness of about 25 µm to about 100 µm, for example a 25 µm thick KAPTON® substrate. Advantageously, a flexible substrate is easy to process and is robust.

Figure 9:
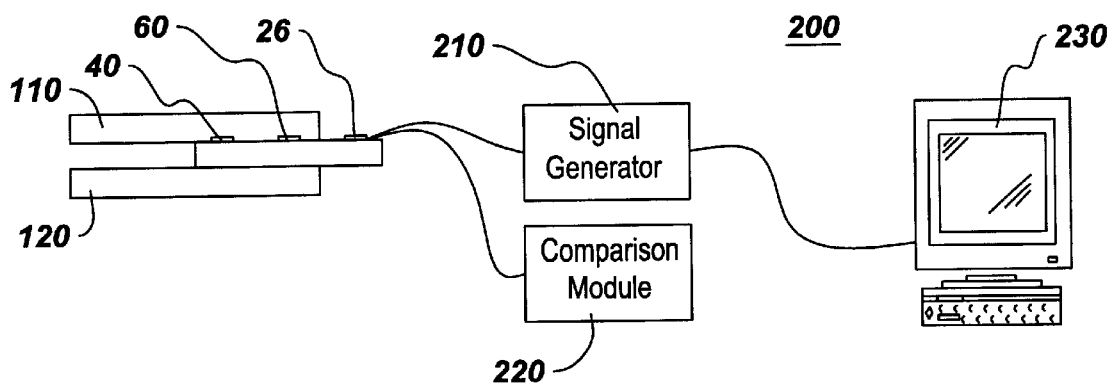
FIG. 9 schematically depicts an embedded eddy current inspection system according to another embodiment of the invention.

Exemplary reference and test coils 60, 40, 42, 140, 142 include single eddy current array probes (SECAPs). SECAPs are single, conducting coils formed on the substrate 20 by known photolithographic methods. A variety of conductive materials, such as copper, silver, and gold are used to form SECAPS. One benefit of SECAPs is that they are compatible with existing eddy current instrumentation, such as an eddy current instrument 220, which is shown in FIG. 9.

Other exemplary reference and test coils 60, 40, 42, 140, 142 are eddy current array probes (ECAPs). ECAPs are arrays of conducting coils (not shown) disposed on the substrate 20. The coils are formed of conductive materials, examples of which include platinum and copper. ECAPs are fabricated using photolithography techniques that are capable of achieving precision and uniformity at small dimensions. An overview of an exemplary fabrication process is provided in commonly assigned U.S. Pat. No. 5,389,876, entitled "Flexible Eddy Current Surface Measurement Array for Detecting Near Surface Flaws in a Conductive Part," by Kristina H. V. Hedengren, et al. An exemplary ECAP includes 24 differential pick up coils which extend approximately 25 mm, with each coil being about 1.8 mm in length and about 0.9 mm in width. Thus, the use of ECAPs accommodates inspecting an area covered by the active area of the array. Exemplary ECAPs further include one and two dimensional arrays of coils.

According to one specific embodiment, the test eddy current coil is an ECAP, and the reference eddy current coil is a SECAP. By configuring the ECAP such that an array of coils (not shown) extends outward from the opening 30, the ECAP can be used to detect crack formation near a fastener, to monitor their propagation from the fastener, and to estimate the crack length.

According to a more specific embodiment, the embedded eddy current inspection apparatus 10 further includes a plurality of pairs of electrical contacts 26 formed on the substrate 20. According to this aspect, a plurality of pairs of leads 28 is formed on the substrate for connecting the reference and the test eddy current coils 60, 40, 42 to the electrical contacts. A pair of contacts and a pair of leads are provided for each reference and test coil.

Figure 4:
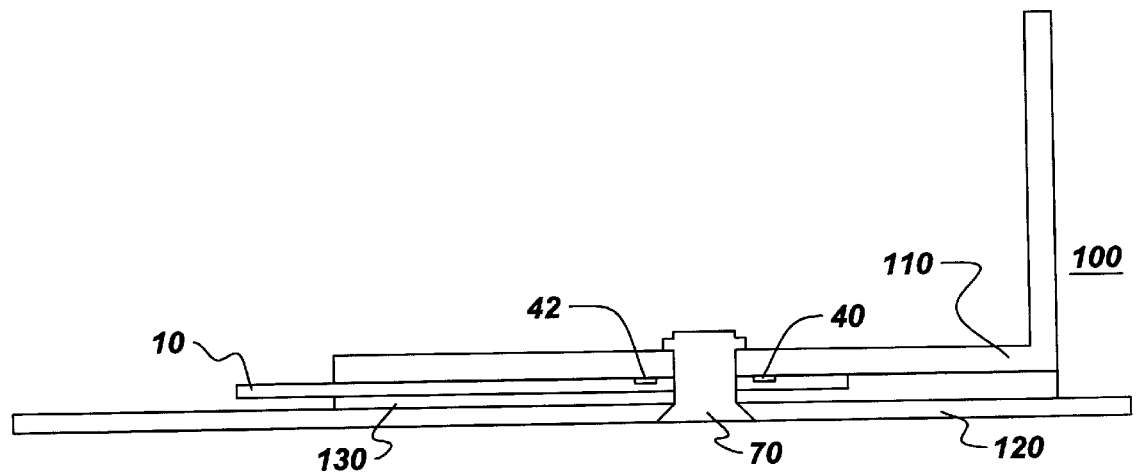
FIG. 4 is a cross-sectional view of a multilayer component structure according to another embodiment of the invention, which includes the embedded inspection apparatus of FIG. 1.
Figure 5:
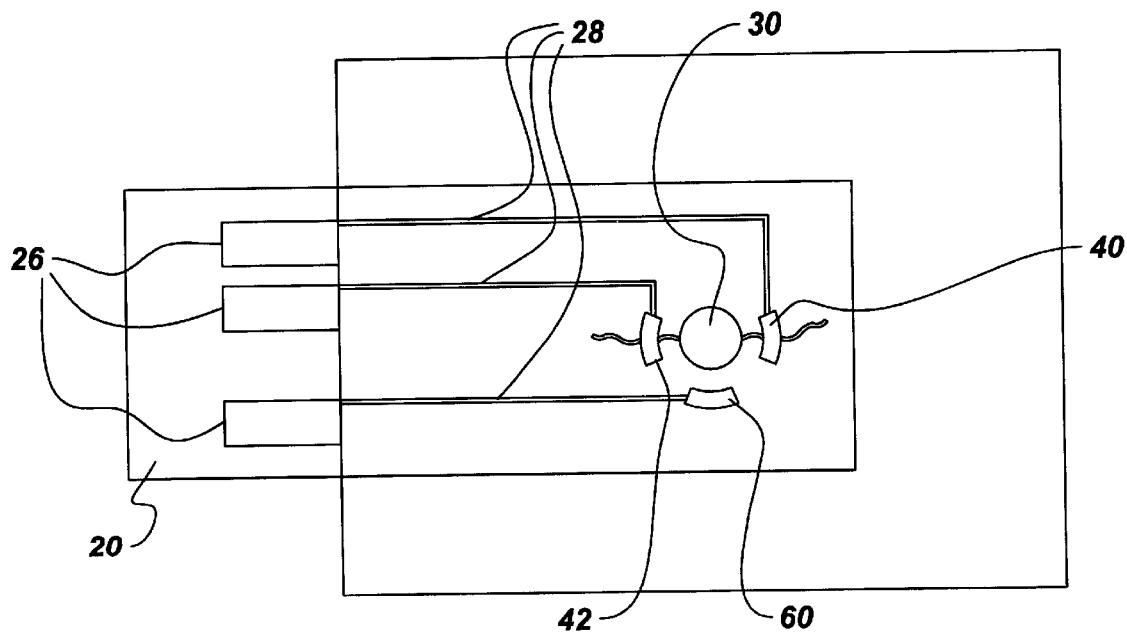
FIG. 5 is a top view of the multilayer component structure shown in FIG. 4, where the upper layer(s) of the component structure have been removed to expose the embedded inspection apparatus.

An internally inspected multilayer component structure 100 embodiment of the invention is illustrated in FIG. 4 in cross-sectional view. A top view of the multilayer component structure is shown in FIG. 5, where the upper layer 110 of the component structure is removed. As the multilayer component structure incorporates many aspects of the embedded inspection apparatus 10, a detailed description of these features will not be repeated.

Figure 7:
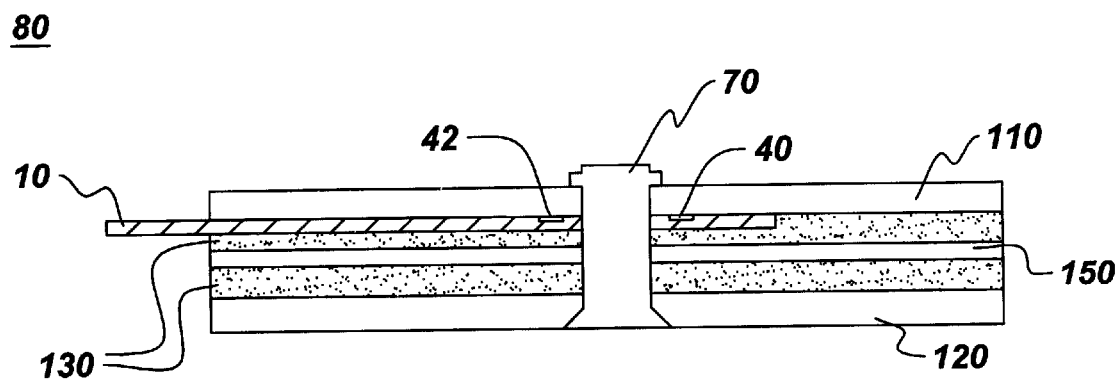
FIG. 7 is a cross-sectional view of a multilayer component structure according to yet another embodiment of the invention.

The internally inspected multilayer component structure 100 includes an upper layer 110 and a lower layer 120, as illustrated in FIG. 4. For multilayer component structures that do not include intermediate layers, either the upper or the lower layer is conductive. Herein, the phrase "conductive layer" means that eddy currents can be generated in the conductive layer. Where the multilayer component structure includes intermediate layers 150, for example as shown in FIG. 7, neither the upper nor the lower layer need be conductive.

The internally inspected multilayer component structure 100 further includes an eddy current probe (also indicated by reference number 10) embedded between the upper and lower layers 110, 120, as illustrated in FIG. 4. The eddy current probe includes the test eddy current coil 40, which faces a subject layer selected from the upper and lower layers. The subject layer is thus the layer being inspected by the test eddy current coil 40. For the configuration illustrated in FIG. 4, the subject layer is the upper layer 110. The subject layer 110 is conductive.

Although the multilayer component structure 100 is illustrated in FIGS. 4 and 5 as including a fastener 70, the multilayer component structure encompasses multilayer component structures held together by other means. Advantageously, the eddy current probe 10 can be embedded between upper and lower layers 110, 120, where the subject layer is difficult to access without disassembling the multilayer component structure. For example, the test coil 40 can be positioned to face any stress point on either of the layers.

According to one embodiment, the eddy current probe 10 further includes the reference eddy current coil 60 positioned in a reference region of the multilayer component structure 100, as illustrated in FIG. 5. The reference coil faces the subject layer 110. The reference region is a region in which cracks are known not to form. As explained above in the description of the first embodiment, cracks 50 in multilayer component structures preferentially form in certain directions based on the stresses on the component structure at fasteners 70 or other stress points. The reference region is selected based on known engineering principles to avoid such crack-prone areas.

Exemplary test and reference coils 40, 60 include SECAPs and ECAPs, as discussed above.

According to another embodiment, the eddy current probe 10 further includes the substrate 20, as for example shown in FIG. 5. As described above, the substrate includes the reference area 22, and the test and reference eddy current coils 40, 60 are affixed to the substrate. The reference coil is positioned in the reference area, which is illustrated in FIG. 2 and described in detail above. Exemplary substrates are formed from a flexible material, such as a flexible organic polymer.

As shown in FIG. 4, a sealant 130 can be disposed between the upper and lower layers 110, 120 and between the substrate 20 and the lower layer, for the component structure shown in FIG. 4. The sealant reduces the collection of corrosive materials in the component structure.

As noted above the multilayer component structure 100 can be held together by means other than the fastener 70. However, according to the embodiment illustrated in FIG. 4, the multilayer component structure includes the fastener. For this embodiment, the substrate 20 has the opening 30 to accommodate the fastener, as illustrated in FIGS. 4 and 5. The test and reference eddy current coils 40, 60 are positioned near the opening, and the fastener extends through the upper and lower layers and through the opening, as illustrated in FIG. 4.

In order to monitor cracks on opposite sides of the fastener, the eddy current probe 10 for another embodiment of the multilayer component structure 100 includes an opposing test eddy current coil 42 positioned across from the test coil 40, as illustrated in FIG. 5 and as discussed above.

In order to monitor crack length, the eddy current probe 10 for yet another embodiment of the multilayer component structure 100 further includes a second test eddy current coil 140 and a second opposing test eddy current coil 142 affixed to the substrate 20 and positioned further from the center of the opening 30 than are the test coil 40 and the opposing test coil 42, respectively, as exemplarily shown in FIG. 3. As discussed above, this arrangement of test coils is advantageous in that it is configured both to detect cracks 50 and to monitor their propagation in the subject layer 110 away from the fastener 70. Further, this principle can be extended to include third, fourth, fifth, etc. sets of test coils (not shown) positioned still further out from the center of the opening, in the manner shown in FIG. 3, depending on the design criteria (i.e., the allowable crack length).

Figure 6:
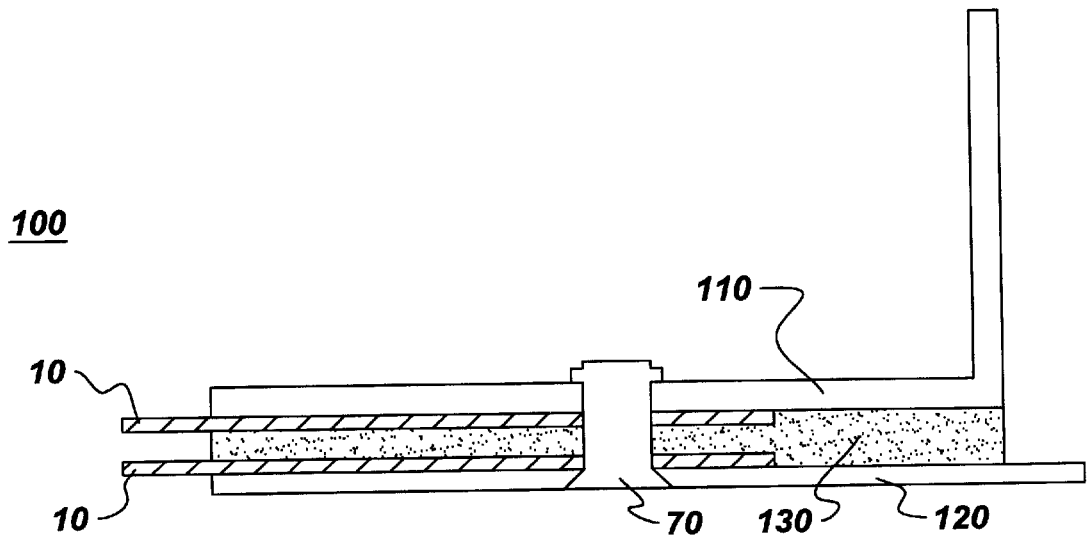
FIG. 6 is a cross-sectional view of a multilayer component structure similar to that shown in FIG. 4, which includes two embedded inspection apparatuses.

The internally inspected multilayer component structure 100 can further be configured to inspect crack formation on both the upper and the lower layers 110, 120, where both layers are conductive. According to this embodiment, the internally inspected multilayer component structure further includes a supplemental eddy current probe (also indicated by reference numeral 10) embedded between the upper and lower layers, as illustrated in FIG. 6. The supplemental eddy current probe is positioned and configured to inspect the remaining layer. For example, if the subject layer coincides with the upper layer 110 (as for the configuration of FIG. 4), the remaining layer is the lower layer 120. Although this numbering scheme is employed for convenience, this embodiment is symmetric in that the multilayer component structure is configured to inspect crack formation in both the upper and lower layers. Accordingly, either layer could be termed the subject or remaining layer.

The supplemental eddy current probe 10 includes a supplemental substrate 20 including a supplemental opening 30 and a supplemental reference area 22, illustrated in FIGS. 1 and 2. As illustrated in FIG. 6, the fastener 70 extends through the supplemental opening. The supplemental eddy current probe further includes supplemental test and reference eddy current coils 40, 60 affixed to the supplemental substrate and facing the remaining layer 120. The supplemental test and reference coils are configured as discussed above with respect to the test and reference coils.

In order to monitor cracks on opposite sides of the fastener 70, the supplemental eddy current probe 10 can further include a supplemental opposing test eddy current coil 42 positioned across from the supplemental test coil 40. As with the embedded inspection apparatus 10 discussed above, the supplemental eddy current probe can include second, third, fourth, etc. pairs (not shown) of test eddy current coils to monitor the length of cracks 50 in the remaining layer 120.

According to yet another embodiment, pairs of electrical contacts 26 are formed on the substrate 20 and on the supplemental substrate 20. The test and reference coils 40, 42, 140, 142, 60 (and supplemental test and reference coils) are connected to the respective pairs of electrical contacts by pairs of leads 28, as illustrated in FIG. 5 (for the substrate).

Figure 8:
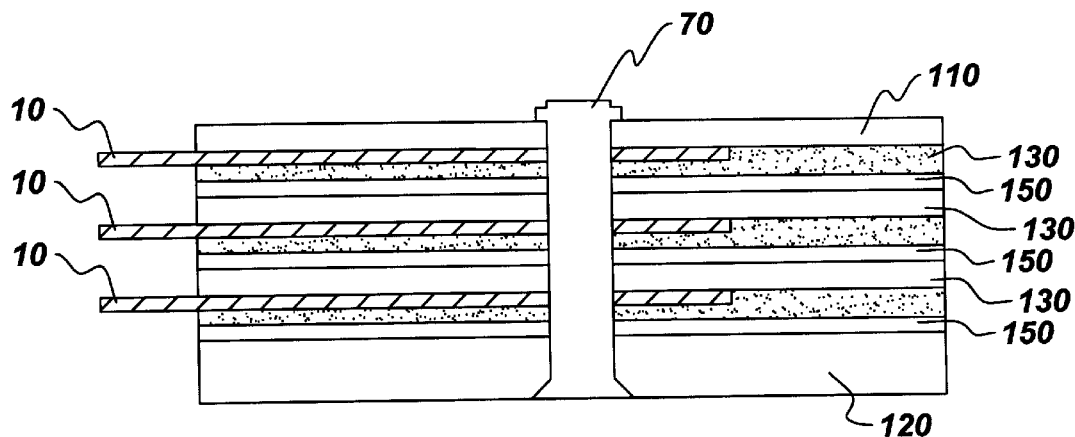
FIG. 8 is a cross-sectional view of a multilayer component structure similar to that shown in FIG. 7, which includes more than one embedded inspection apparatuses.

An internally inspected multilayer component structure 80, as shown for example in FIGS. 7 and 8 is similar to the multilayer component structure 100 in many aspects. Accordingly, only features of the multilayer component structure not previously will be discussed in detail. As exemplarily illustrated in FIG. 7, the multilayer component structure 80 includes an upper layer 110, at least one intermediate layer 150, and a lower layer 120. The multilayer component structure further includes the eddy current probe 10 embedded between a pair of adjacent layers selected from the lower, intermediate and upper layers. For example, for the component structure shown in FIG. 7, the pair of adjacent layers comprises the upper layer and the intermediate layer. The eddy current probe includes the test coil 40 facing a subject layer selected from the pair of adjacent layers. For the component structure shown in FIG. 7, the subject layer is the upper layer. For convenience.the subject layer will be designated by the same reference number 110. However, in general the subject layer can comprise any conductive layer of the component structure.

The eddy current probe 10 is discussed above and previous descriptions will not be repeated in detail. According to one embodiment of the multilayer component structure 80, the eddy current probe 10 further includes the reference eddy current coil 60 facing the subject layer (110 for the structure of FIG. 7).

According to another embodiment of the multilayer component structure 80, the eddy current probe 10 further includes the substrate 20 having the opening 30 and the reference area 22. The multilayer component structure further includes the fastener 70 extending through the upper, intermediate, and lower layers 110, 150, 120 and through the opening, as shown in FIG. 7.

To monitor cracks on opposite sides of the fastener 70, the eddy current probe 10 for another embodiment of the multilayer component structure 80 further includes the opposing test current coil 42 positioned across from the test eddy current coil 40, as exemplarily shown in FIG. 7.

The internally inspected multilayer component structure 80 of the third embodiment encompasses the case of a plurality of intermediate layers 150 and a plurality of eddy current probes 10, as exemplarily shown in FIG. 8. In addition, second, third, fourth, etc. pairs of test coils can be included on each of the eddy current probes 10 to monitor crack propagation away from the fastener in the subject layers(s).

Because the internally inspected multilayer component structures 100, 80 incorporate embedded eddy current probes 10, these multilayer component structures are suitable for in flight monitoring of crack formation in aircraft structures. Namely, by incorporating the multilayer component structures into an aircraft structure, eddy current inspection can be performed at any time during the life of the aircraft structure, including during flight operations. This provides a distinct advantage relative to conventional eddy current inspection techniques, which require disassembly and re-assembly of the aircraft structure.

An inspection method embodiment of the invention for inspecting a multilayer component structure 100, including an upper and a lower layer 110, 120, is discussed with respect to FIGS. 4 and 5. The inspection method includes energizing the test eddy current coil 40 embedded between the upper and lower layers. The test coil faces a subject layer selected from the upper and lower layers. As discussed above, for the component structure of FIGS. 4 and 5, the subject layer is the upper layer 110. The inspection method further includes energizing the reference coil 60 simultaneously with the test coil 40 to obtain the reference signal. The reference coil is discussed above. A test signal from the test coil is compared with a reference signal from the reference coil to determine whether a flaw is present in the subject layer near the test eddy current coil. More precisely, a difference signal is obtained by subtracting the reference and the test signals. Reference and test coils that are in electrical balance (i.e., a difference signal is obtained that is approximately zero to within the precision of the measurements), indicate that there is no flaw near the test coil. When the reference and test coils are out of balance (i.e., a nonzero difference signal is obtained), a flaw near the test coil is indicated.

According to another embodiment, the test and reference coils 40, 60 are positioned near the fastener 70 extending through the upper and lower layers 110, 120.

In order to monitor crack length, the inspection method according to another embodiment further includes energizing the opposing test coil 42, the second test coil 140, and the second opposing test coil 142, which are discussed above. Each of the opposing, second, and second opposing test coils is energized simultaneously with the reference coil 60. However, the test coils are energized sequentially, with the reference coil being energized each time one of the test coils is energized. A test signal from the opposing test coil is compared with a reference signal from the simultaneously energized reference coil to determine whether a flaw 50 is present in the subject layer (110 in FIG. 4) near the opposing test eddy current coil. In this manner, a difference signal is obtained. A nonzero difference signal indicates the presence of a flaw near the opposing test eddy current coil. A test signal from the second test coil is also compared with a reference signal obtained from the simultaneous energizing of the reference coil to determine whether the flaw in the subject layer near the test coil extends to the second test coil. The comparison produces a difference signal, and a nonzero difference signal indicates the presence of a flaw near the second test coil. In addition, a test signal from the second opposing test coil is compared with a reference signal obtained from the simultaneous energizing of the reference coil to determine whether the flaw near the opposing test coil extends to the second opposing test coil. The comparison produces a difference signal, which if nonzero, indicates the presence of a flaw near the second opposing test coil.

An assembly method embodiment of the invention for assembling an internally inspected multilayer component structure 100 is described with respect to FIGS. 4 and 5. The assembly method includes embedding the eddy current probe 10 between the upper and the lower layer 110, 120 of the multilayer component structure, such that the test coil 40 faces the subject layer selected from the upper and lower layers. As discussed above, for the component structure of FIG. 4, the subject layer is the upper layer 110.

According to one embodiment of the assembly method, the eddy current probe 10 further includes the reference eddy current coil 60, as discussed above.

To accommodate the fastener 70, according to another embodiment the test and reference coils 40, 60 are affixed to the substrate 20 with the opening 30 and the reference area 22, as discussed above and as exemplarily shown in FIG. 5. The assembly method of this embodiment further includes extending the fastener 70 through the upper and lower layers and through the opening of the substrate.

As discussed above, a sealant 130 can be disposed between the upper and lower layers 110, 120 to reduce the collection of corrosive materials in the component structure 100.

Advantageously, by embedding the eddy current probe 10 in the multilayer component structure 100, inaccessible conductive layers of the component structure can be inspected without requiring disassembly of the component structure.

To monitor cracks on opposite sides of the fastener 70, according to another embodiment of the assembly method the eddy current probe 10 further includes the opposing test eddy current coil 42, as discussed above.

To monitor crack length, the eddy current probe 10 according to yet another embodiment of the assembly method further includes the second test eddy current coil 140 and the second opposing test eddy current coil 142. Advantageously, this arrangement is configured to detect cracks, monitor their propagation from the fastener, and estimate the crack length.

An embedded eddy current inspection system 200 embodiment of the invention includes the eddy current probe 10 embedded between the upper and the lower layer 110, 120, as exemplarily illustrated in FIG. 9. The eddy current probe includes the test eddy current coil 40. Exemplary test coils include SECAPs and ECAPs. The embedded eddy current inspection system further includes a signal generator 210, as schematically illustrated in FIG. 9, for energizing the test coil. An exemplary signal generator supplies an AC signal. SECAP and ECAP coils are energized by signals having amplitudes of about 5V to about 10 V and frequencies in the range of about 500 KHz to about 6 MHz.

The embedded inspection system 200 further includes a comparison module 220, for comparing a signal received from the test coil 40 with a reference signal and outputting a compared signal. One exemplary comparison module is an eddy current instrument (also indicated by reference number 220).

According to embodiment of the embedded eddy current inspection system 200, the eddy current probe 10 further includes the reference eddy current coil 60. Exemplary reference coils include SECAPs and ECAPs. The reference coil is energized by the signal generator simultaneously with the test coil 40 and supplies the reference signal(s) to the comparison module.

According to a more specific embodiment, the embedded inspection system 200 further includes a computer 230, as illustrated in FIG. 9. The computer is configured to control the signal generator 210.

Advantageously, the embedded inspection system 200 can be used to inspect otherwise inaccessible conductive layers of a multilayer component structure 100 without requiring disassembly of the component structure. Consequently, the embedded inspection system permits repeated eddy current inspection of lap joints and other component structures including rivets or other fasteners or stress points, without requiring time, money, and labor intensive disassembly of the overall structure, such as an aircraft.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method of inspecting a multilayer component structure including an upper, a lower layer and at least one intermediate layer situated between the upper and lower layers, said method comprising:

energizing a test eddy current (EC) coil embedded between the upper and intermediate layers, the test EC coil facing an upper subject layer of the multilayer component structure, the upper subject layer being one of the upper or intermediate layers;

energizing a reference EC coil simultaneously with the test EC coil, the reference EC coil being embedded between the upper and the intermediate layers in a reference region of the multilayer structure and facing the upper subject layer;

comparing a test signal from the test EC coil with a reference signal from the reference EC coil to determine whether a flaw is present in the upper subject layer near the test EC coil;

energizing a supplemental test EC coil embedded between the intermediate and lower layers, the supplemental test EC coil facing a lower subject layer of the multilayer component structure, the lower subject layer being one of the intermediate or lower layers;

energizing a supplemental reference EC coil simultaneously with the supplemental test coil, the supplemental reference EC coil being embedded between the intermediate and the lower layers in a reference region of the multilayer structure and facing the lower subject layer; and comparing a test signal from the supplemental test EC coil with a reference signal from the supplemental reference EC coil to determine whether a flaw is present in the lower subject layer near the supplemental test EC coil.

2. The inspection method of claim 1, wherein the test and reference EC coils and the supplemental test and reference EC coils are positioned near a fastener extending through the upper, intermediate and lower layers.

3. The inspection method of claim 2 further comprising:

energizing an opposing test EC coil and the reference EC coil simultaneously, the opposing test EC coil being embedded between the upper and intermediate layers, facing the upper subject layer, and positioned across from the test EC coil;

energizing a second test EC coil and the reference EC coil simultaneously, the second test EC coil being embedded between the upper and intermediate layers, facing the upper subject layer, and positioned further from a center of the opening than is the test EC coil;

energizing a second opposing test EC coil and the reference EC coil simultaneously, the second opposing test EC coil being embedded between the upper and intermediate layers, facing the subject layer, and positioned further from the center of the opening than is the opposing test EC coil;

comparing a test signal from the opposing test EC coil with a reference signal from said simultaneous energizing of the reference EC coil to determine whether a flaw is present in the subject layer near the opposing test EC coil;

comparing a test signal from the second test EC coil with a reference signal from said simultaneous energizing of the reference EC coil to determine whether the flaw in the subject layer near the test EC coil extends to the second test EC coil; and comparing a test signal from the second opposing test EC coil with a reference signal from said simultaneous energizing of the reference EC coil to determine whether the flaw in the subject layer near the opposing test EC coil extends to the second opposing test EC coil.

4. The inspection method of claim 2 further comprising:

energizing a supplemental opposing test EC coil and the supplemental reference EC coil simultaneously, the supplemental opposing test EC coil being embedded between the intermediate and lower layers, facing the lower subject layer, and positioned across from the supplemental test EC coil;

energizing a second supplemental test EC coil and the supplemental reference EC coil simultaneously, the second supplemental test EC coil being embedded between the intermediate and lower layers, facing the supplemental subject layer, and positioned further from a center of the opening than is the supplemental test EC coil;

energizing a second supplemental opposing test EC coil and the supplemental reference EC coil simultaneously, the second supplemental opposing test EC coil being embedded between the intermediate and lower layers, facing the lower subject layer, and positioned further from the center of the opening than is the supplemental opposing test EC coil;

comparing a test signal from the supplemental opposing test EC coil with a reference signal from said simultaneous energizing of the supplemental reference EC coil to determine whether a flaw is present in the lower subject layer near the supplemental opposing test EC coil;

comparing a test signal from the second supplemental test EC coil with a reference signal from said simultaneous energizing of the supplemental reference EC coil to determine whether the flaw in the lower subject layer near the supplemental test EC coil extends to the second supplemental test EC coil; and comparing a test signal from the second supplemental opposing test EC coil with a reference signal from said simultaneous energizing of the supplemental reference EC coil to determine whether the flaw in the lower subject layer near the supplemental opposing test EC coil extends to the second supplemental opposing test EC coil.

5. A method of assembling an internally inspected multilayer component structure comprising an upper and a lower layer and at least one intermediate layer disposed between the upper and lower layers, said method comprising:

embedding an eddy current (EC) probe between the upper and intermediate layers, the EC probe comprising a test EC coil facing an upper subject layer, the upper subject layer being one of the upper or intermediate layers; and embedding a supplemental EC probe between the intermediate and lower layers, the supplemental EC probe comprising a supplemental test EC coil facing a lower subject layer, the lower subject layer comprising one of the intermediate and lower layers.

6. The assembly method of claim 5, wherein the EC probe further comprises a reference EC coil positioned in a reference region of the multilayer component structure and facing the subject layer, and wherein the supplemental EC probe further comprises a supplemental reference EC coil positioned in the reference region of the multilayer component structure and facing the lower subject layer.

7. The assembly method of claim 6, wherein each of the EC probe and the supplemental EC probe further comprises a substrate having an opening and a reference area, the test and reference EC coils and the supplemental test and reference EC coils being affixed to the respective one of the substrates and positioned near the respective one of the openings, and the reference and supplemental reference EC coils being positioned in the respective one of the reference areas, said method further comprising:

extending a fastener through the upper, intermediate and lower layers and through the respective openings of the substrates.

8. The assembly method of claim 7, wherein the EC probe further comprises an opposing test EC coil affixed to the respective substrate, facing the upper subject layer, and positioned near the respective opening and across from the test EC coil, and wherein the supplemental EC probe further comprises a supplemental opposing test EC coil affixed to the respective one of the substrates, facing the lower subject layer, and positioned near the respective one of the openings and across from the supplemental test EC coil.

9. The assembly method of claim 8, wherein the EC probe further comprises a second test EC coil and a second opposing test EC coil affixed to the respective substrate, facing the upper subject layer, and positioned further from a center of the respective opening than are the test and the opposing test EC coils, respectively, and wherein the supplemental EC probe further comprises a second supplemental test EC coil and a second supplemental opposing test EC coil affixed to the respective substrate, facing the lower subject layer, and positioned further from a center of the respective opening than are the supplemental test and supplemental opposing test EC coils, respectively.

10. An internally inspected multilayer component structure comprising:

an upper layer;

a lower layer;

at least one intermediate layer disposed between said upper and lower layers;

an eddy current (EC) probe embedded between said upper and intermediate layers, said EC probe comprising a test EC coil facing an upper subject layer, said upper subject layer being one of said upper and intermediate layers; and a supplemental EC probe embedded between said intermediate and lower layers, said supplemental EC probe comprising a supplemental test EC coil facing a lower subject layer, said lower subject layer being one of said intermediate and lower layers.

11. The internally inspected multilayer component structure of claim 12, wherein said EC probe further comprises a reference EC coil facing said upper subject layer and positioned in a reference region of said multilayer component structure, and wherein said supplemental EC probe further comprises a supplemental reference EC coil facing said lower subject layer and positioned in the reference region of said multilayer component structure.

12. The internally inspected multilayer component structure of claim 11, wherein each of said EC probe and said supplemental EC probe further comprises:

a substrate including a reference area, wherein said test and reference EC coils and said supplemental test and reference EC coils are affixed to the respective one of said substrates, and wherein said reference EC coil and said supplemental reference EC coil are positioned in the respective one of said reference areas.

13. The internally inspected multilayer component structure of claim 12, wherein each of said EC probe and said supplemental EC probe further comprises:

a plurality of pairs of electrical contacts formed on a respective one of said substrates; and a plurality of pairs of leads formed on the respective one of said substrates, each pair of leads connecting a respective one of said reference and supplemental reference EC coils and said test and supplemental test EC coils to a respective pair of said electrical contacts.

14. The internally inspected multilayer component structure of claim 13, wherein each of said substrates comprises a flexible organic polymer.

15. The internally inspected multilayer component structure of claim 12, wherein said test and supplemental test EC coils and said reference and supplemental reference EC coils comprise single EC array probes (SECAPs).

16. The internally inspected multilayer component structure of claim 12, wherein said test and supplemental test EC coils and said reference and supplemental reference EC coils comprise EC array probes (ECAPs).

17. The internally inspected multilayer component structure of claim 12, wherein each of said test and supplemental test EC coils comprises an ECAP and each of said reference and supplemental reference EC coils comprises a SECAP.

18. The internally inspected multilayer component structure of claim 12, wherein each of said substrates has an opening, said test and reference and supplemental test and reference EC coils being positioned near said respective opening, said internally inspected multilayer component structure further comprising:

a fastener extending through said upper, intermediate and lower layers and through said openings.

19. The internally inspected multilayer component structure of claim 18, wherein said EC probe further comprises an opposing test EC coil affixed to said respective substrate near said respective opening, said opposing test EC coil being positioned across from said test EC coil, wherein said supplemental EC probe further comprises a supplemental opposing test EC coil affixed to said respective substrate near said respective opening, said supplemental opposing test EC coil being positioned across from said supplemental test EC coil.

20. The internally inspected multilayer component structure of claim 19, wherein said EC probe further comprises:

a second test EC coil affixed to said respective substrate and positioned further from a center of said respective opening than is said test EC coil; and a second opposing test EC coil affixed to said respective substrate and positioned further from a center of said respective opening than is said opposing test EC coil, and wherein said supplemental EC probe further comprises:

a second supplemental test EC coil affixed to said respective substrate and positioned further from a center of said respective opening than is said supplemental test EC coil; and second supplemental opposing test EC coil affixed to said respective substrate and positioned further from a center of said respective opening than is said supplemental opposing test EC coil.

21. An embedded eddy current inspection system for inspecting a multilayer component structure comprising an upper and a lower layer and at least one intermediate layer disposed between the upper and lower layers, said system comprising:

an eddy current probe embedded between the upper and intermediate layers, said eddy current probe comprising at least one test eddy current coil facing a conductive layer within the multilayer component structure and configured to acquire a test signal from the conductive layer;

a supplemental eddy current probe embedded between the intermediate and lower layers, said supplemental eddy current probe comprising at least one supplemental test eddy current coil facing a supplemental conductive layer within the multilayer component structure and configured to acquire a supplemental test signal from the supplemental conductive layer;

a signal generator configured to energize said test and said supplemental test eddy current coils; and a comparison module for comparing the test signal received from said test eddy current coil with a reference signal and outputting a compared signal and for comparing the test signal received from said supplemental test eddy current coil with a supplemental reference signal and outputting a supplemental compared signal.

22. The embedded eddy current inspection system of claim 21, wherein said eddy current probe further comprises a reference eddy current coil configured to supply the reference signal, wherein said signal generator is further configured to energize said test and reference eddy current coils simultaneously, wherein said supplemental eddy current probe further comprises a supplemental reference eddy current coil configured to supply the supplemental reference signal, and wherein said signal generator is further configured to energize said supplemental test and reference eddy current coils simultaneously.

23. The embedded inspection system of claim 22, further comprising a computer configured to control said signal generator.

* * * * *

UNITED STATES PATENT AND TRADEMARK OFFICE
CERTIFICATE OF CORRECTION

PATENT NO.     : 6,545,469 B1
DATED          : April 8, 2003
INVENTOR(S)    : Thomas James Batzinger et al.

It is certified that error appears in the above-identified patent and that said Letters Patent is hereby corrected as shown below:

Column 13,
Line 58, reads "ture of claim 12, wherein said EC probe further comprises" should read -- ture of claim 10, wherein said EC probe further comprises --

Signed and Sealed this

Twenty-sixth Day of October, 2004

JON W. DUDAS
*Director of the United States Patent and Trademark Office*